US012708771B2

(12) United States Patent
Nuyujukian et al.

(10) Patent No.: US 12,708,771 B2
(45) Date of Patent: Aug. 18, 2026

(54) SYSTEMS AND METHODS FOR SEIZURE DETECTION USING COMPRESSION-ENABLED JOINT ENTROPY ESTIMATION

(71) Applicant: The Board of Trustees of the Leland Stanford Junior University, Stanford, CA (US)

(72) Inventors: Paul Nuyujukian, Stanford, CA (US); Lisa Yamada, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 519 days.

(21) Appl. No.: 18/295,179

(22) Filed: Apr. 3, 2023

(65) Prior Publication Data

US 2023/0310857 A1 Oct. 5, 2023

Related U.S. Application Data

(60) Provisional application No. 63/362,388, filed on Apr. 1, 2022.

(51) Int. Cl.
*A61N 1/36* (2006.01)

(52) U.S. Cl.
CPC ..... *A61N 1/36064* (2013.01); *A61N 1/36139* (2013.01)

(58) Field of Classification Search
CPC .. A61N 1/36064; A61N 1/36139; A61B 5/37; A61B 5/7232; A61B 5/374; A61B 5/4094; A61B 5/4836
See application file for complete search history.

(56) References Cited

U.S. PATENT DOCUMENTS

2021/0259621 A1* 8/2021 Alves ........................ A61B 7/00
2021/0346709 A1* 11/2021 Leyde .................. A61B 5/4836

OTHER PUBLICATIONS

Aung et al., "Modified-Distribution Entropy as Features for the Detection of Epileptic Seizures", Frontiers in Physiology, vol. 11, No. 607, Jun. 2020, 10 pgs., doi: 10.3389/fphys.2020.00607.
Dao et al., "Lossy Compression Techniques for EEG Signals", IEEE 2015 International Conference on Advanced Technologies for Communications, ATC, Conference Date: Oct. 14-16, 2015, Ho Chi Minh, Vietnam, DOI: 10.1109/ATC.2015.7388309, 6 pgs.
Kannathal et al., "Entropies for detection of epilepsy in EEG", ScienceDirect, vol. 80, Issue 3, Dec. 2005, pp. 187-194.

(Continued)

*Primary Examiner* — Michael J Carey
(74) *Attorney, Agent, or Firm* — KPPB LLP

(57) ABSTRACT

Systems and methods for seizure detection in accordance with embodiments of the invention are illustrated. One embodiment includes an automated seizure treatment system, including an electroencephalogram (EEG) device configured to record neural activity from a brain of a patient, a treatment device, a processor, and a memory, the memory containing a seizure detection application that configures the processor to obtain an EEG signal from the EEG device, calculate an inverse compression ratio based on the EEG signal, and when the inverse compression ratio is greater than a classification threshold, deliver treatment capable of stopping the seizure to the patient using the treatment device.

18 Claims, 3 Drawing Sheets

(56) References Cited

OTHER PUBLICATIONS

Nguyen et al., “A Study of Combined Lossy Compression and Seizure Detection on Epileptic EEG Signals”, ScienceDirect, Procedia Computer Science, vol. 126, 2018, pp. 156-165.
Wu et al., “Detecting Epileptic Seizures in EEG Signals with Complementary Ensemble Empirical Mode Decomposition and Extreme Gradient Boosting”, Entropy 2020, vol. 22, No. 2, 2020, 25 pgs, doi: 10.3390/e22020140.
Yamada et al., “Seizure Detection and Localization Using Human Intracranial Electrophysiology via Information Theoretic Methods”, Wu Tsai Neurosciences Institute, Stanford University, 2021.
Zbili et al., “A quick and easy wa y to estimate entropy and mutual information for neuroscience”, bioRxiv preprint, Jan. 31, 2021, doi: 10.1101/2020.08.04.236174, 33 pgs.
Zeng et al., “Automatic detection of absence seizures with compressive sensing EEG”, Neurocomputing, vol. 171, 2016, pp. 497-502, doi:10.1016/j.neucom.2015.06.076.

* cited by examiner

SYSTEMS AND METHODS FOR SEIZURE DETECTION USING COMPRESSION-ENABLED JOINT ENTROPY ESTIMATION

CROSS-REFERENCE TO RELATED APPLICATIONS

The current application claims the benefit of and priority under 35 U.S.C. § 119(e) to U.S. Provisional Patent Application No. 63/362,388 entitled "Systems and Methods for Seizure Detection Using Compression-Enabled Joint Entropy Estimation" filed Apr. 1, 2022. The disclosure of U.S. Provisional Patent Application No. 63/362,388 is hereby incorporated by reference in its entirety for all purposes.

FIELD OF THE INVENTION

The present invention generally relates to entropy-based seizure detection.

BACKGROUND

There are many ways to measure neural activity. Electroencephalography (EEG) is a recording modality that records neural activity as an electrogram. There are several different forms of EEG. The non-invasive form is called "scalp EEG" or sometimes just "EEG" and involves placement of electrodes on the scalp of a patient. Intracranial EEG involves surgical placement of electrodes under the skull. Compared to scalp EEG, it has higher spatial and temporal resolution, as well as higher signal-to-noise ratio because the skull causes attenuation of the electric potentials in the brain. One form of intracranial EEG is electrocorticography (ECoG) which uses strips and grids of electrodes on the surface of the brain. Another form of intracranial EEG is stereoelectroencephalography (stereo-EEG, sEEG), which involves a minimally invasive procedure to instrument depth electrodes directly into the brain. Both forms of intracranial EEG are used to localize the focus of epileptic seizures.

A seizure is a sudden, uncontrolled burst of electrical activity in the brain. There are many different types of seizures which can cause mild to severe symptoms. Symptoms can be cognitive and/or motor, which in turn can cause secondary injuries. Epilepsy is a broad term used for a brain disorder that causes seizures.

In the context of information theory, entropy is a measure of information in a random variable. Joint entropy is a measure of the total information associated with a set of variables.

SUMMARY OF THE INVENTION

Systems and methods for seizure detection in accordance with embodiments of the invention are illustrated. One embodiment includes an automated seizure treatment system, including an electroencephalogram (EEG) device configured to record neural activity from a brain of a patient, a treatment device, a processor, and a memory, the memory containing a seizure detection application that configures the processor to obtain an EEG signal from the EEG device, calculate an inverse compression ratio based on the EEG signal, and when the inverse compression ratio is greater than a classification threshold, deliver treatment capable of stopping the seizure to the patient using the treatment device.

In a further embodiment, to calculate inverse compression ratio, the seizure detection application further configures the processor to measure an uncompressed size of the EEG signal, compress the EEG signal using a lossless compression algorithm, measure a compressed size of the EEG signal, and divide the compressed size by the uncompressed size.

In still another embodiment, the EEG device is a stereo EEG device.

In a still further embodiment, the EEG device is a scalp EEG device.

In yet another embodiment, the EEG device is an electrocorticogram (ECoG) device.

In a yet further embodiment, the treatment device is an implantable neurostimulator configured to produce neurostimulation to counteract the spread of seizure activity in the brain of the patient.

In another additional embodiment, the treatment device is a drug pump configured to deliver an anti-seizure drug.

In a further additional embodiment, the treatment device further includes a warning device capable of producing an alert indicating seizure activity.

In another embodiment again, the classification threshold is a value selected to maximize an F1 score for a precision recall curve generated using historical EEG signals from the brain of the patient.

In a further embodiment again, the seizure detection application further directs the processor to obtain several EEG signals from the EEG device, where each EEG signal in the several signals is recorded at a different electrode of the EEG device, and the inverse compression ratio is calculated based on the EEG signal and the several EEG signals.

One embodiment includes an automated seizure treatment method, including obtaining an EEG signal from an EEG device configured to record neural activity from a brain of a patient, calculating an inverse compression ratio based on the EEG signal using a seizure detector, and when the inverse compression ratio is greater than a classification threshold, automatically delivering treatment capable of stopping the seizure to the patient using the treatment device.

In still yet another embodiment, calculating inverse compression ratio includes measuring an uncompressed size of the EEG signal, compressing the EEG signal using a lossless compression algorithm, measuring a compressed size of the EEG signal, and dividing the compressed size by the uncompressed size.

In a still yet further embodiment, the EEG device is a stereo EEG device.

In still another additional embodiment, the EEG device is a scalp EEG device.

In a still further additional embodiment, the EEG device is an ECoG device.

In still another embodiment again, the treatment device is an implantable neurostimulator configured to produce neurostimulation to counteract the spread of seizure activity in the brain of the patient.

In a still further embodiment again, the treatment device is a drug pump configured to deliver an anti-seizure drug.

In yet another additional embodiment, the treatment device further includes a warning device capable of producing an alert indicating seizure activity.

In a yet further additional embodiment, the classification threshold is a value selected to maximize an F1 score for a precision recall curve generated using historical EEG signals from the brain of the patient.

In yet another embodiment again, the method further includes steps for obtaining several EEG signals from the EEG device, where each EEG signal in the several signals is recorded at a different electrode of the EEG device, and calculating the inverse compression ratio based on the EEG signal and the several EEG signals.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
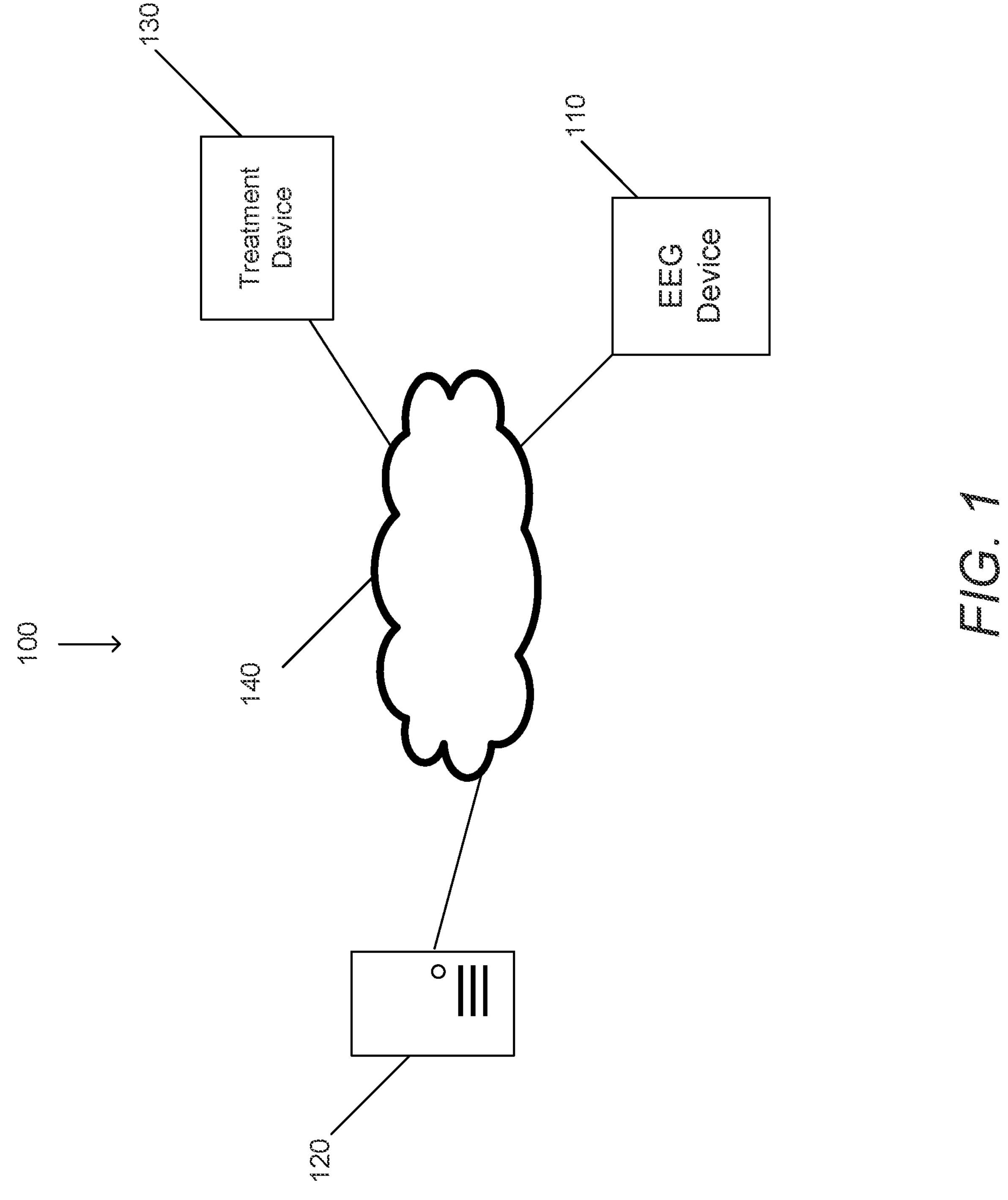
FIG. 1 is a seizure detection system in accordance with an embodiment of the invention.

Affecting over 50 million people worldwide, epilepsy ranks fourth in severity (i.e. quality of life impairment), among 220 health conditions of the Global Burden of Disease project. Approximately 33% of patients have refractory epilepsy and face limited seizure management alternatives, often having to turn to surgical interventions like resective and/or ablative epilepsy surgery. Further, the clinical standard of epilepsy assessment relies on manual review of electroencephalograms (EEGs) by epileptologists, which is time and labor intensive, as well as highly subjective, resulting in variability in treatment even when a patient has access to a healthcare provider.

In order to better serve the patient population, there is a need for quantitative EEG (qEEG) methods where EEG data is automatically and reliably processed in order to resolve these issues. Automated qEEG methods can be used in batch processing of EEG to facilitate the manual review of epileptologists. Attempts at developing qEEG methods have not yet been able to achieve the same level of performance as human specialists in clinics and are meant to be used to augment human clinicians. Real-time automated qEEG methods can be used for device-related therapies to actively respond to seizures.

In many embodiments, systems and methods described herein can detect seizures reliably in an automated, model-free fashion. In various embodiments, systems and methods described herein can be used to facilitate epileptologist review in an automated fashion. In many embodiments, near real-time automated detection can trigger immediate, automated interventions in a closed-loop response. When a seizure is detected, an immediate goal is to stop the spread of abnormal electrical activity. This can be achieved using any of a variety of electronic or pharmaceutical means. For example, implantable neuromodulators can be used to disrupt the spread of neural activity. Pharmaceuticals can be delivered via an on-demand mechanism such as (but not limited to) drug pumps and wireless nanoparticle delivery to halt the spread. Example drugs include (but are not limited to) diazepam, midazolam, clonazepam, and lorazepam.

In order to achieve near real-time identification of seizures, computational efficiency can provide a significant advantage. From an information theory perspective, periods of seizure activity (i.e., abnormal, excessive, and synchronous neuronal activity in the brain) have different amounts of entropy than periods of non-seizure activity. Systems and methods described herein utilize an inverse compression ratio (ICR) metric to measure the amount of entropy in an EEG in a computationally efficient manner in order to identify the presence of seizure in both single-electrode and multielectrode EEG. Calculation and use of ICR are discussed in further detail following a discussion of seizure detection systems.

Seizure Detection Systems

Seizure detection systems are capable of obtaining EEG signals from a patient and processing them to identify seizures in batch processing and/or near real-time. In many embodiments, seizure detection systems include treatment devices which are triggered automatically to stop the spread of the seizure activity in the brain when the seizure is detected. In numerous embodiments, seizure detection systems can be fully mobile, that is a patient can be ambulatory and/or go about their day while wearing and/or being connected to the system. In various embodiments, seizure detection systems are designed to be used with stationary patients, for example a patient in a hospital bed. Further, many different EEG modalities can be used such as (but not limited to) scalp EEG, electrocorticography (ECoG), stereo-EEG, and/or any other EEG recording modality as appropriate to the requirements of specific applications of embodiments of the invention.

Turning now to FIG. 1, a seizure detection system in accordance with an embodiment of the invention is illustrated. Seizure detection system 100 includes an EEG device 110. EEG devices are devices which can record EEG signals from a patient's brain. As noted above, many different modalities of EEG can be used, and similarly many different EEG devices can be used as appropriate to the requirements of specific applications of embodiments of the invention. For example, in various embodiments, scalp EEG headsets are used as the EEG device. In many embodiments, ECoG electrodes are used as part of an EEG device which can provide an EEG signal. In numerous embodiments, stereo-EEG electrodes are implanted and used as the EEG device. EEG devices may include electrodes as well as other communication components in order to retrieve and provide the signal from the electrodes.

Seizure detection system 100 further includes a seizure detector 120. Seizure detectors are computational devices capable of carrying out seizure detection processes as described herein. In numerous embodiments, seizure detectors are computers such as desktops or laptops. However, seizure detectors can be implemented using any number of different computing hardware including (but not limited to)

tablet computers, smartphones, smart watches, servers, cloud computing systems, and/or any other computational platform as appropriate to the requirements of specific applications of embodiments of the invention.

Seizure detection system 100 further includes a treatment device 130. The type of treatment device can be modified as to the specific needs of a given patient. In numerous embodiments, the treatment device is a device which can stop the spread of seizure. Example treatment devices include (but are not limited to) neurostimulators, and drug pumps. In some embodiments, treatment devices act as warning devices such as speakers, vibration devices, lights, and/or any other device capable of signaling the presence of seizure activity. As can be readily appreciated, more than one treatment device and/or warning device can be utilized as appropriate to the requirements of specific applications of embodiments of the invention.

Seizure detection system 100 includes a network 140. Network 140 enables data transfer between EEG device 110, seizure detector 120, and treatment device 130. In some embodiments, different networks are used to connect different components. Networks can be implemented using wireless communication, wired communication, or any combination thereof. As can be readily appreciated, while a particular system architecture is illustrated in FIG. 1, any number of different architectures can be used as appropriate to the requirements of specific applications of embodiments of the invention. For example, different computational devices can be introduced to provide access to medical professionals, or otherwise integrate with different medical systems. In various embodiments, multiple EEG devices may be used. Seizure detectors are discussed in further detail below.

Seizure Detectors

As noted above, seizure detectors are computing devices which are capable of processing EEG signals and detecting the presence of seizure in near real-time or with batch processing. Seizure detectors receive patient EEG signals and process them to calculate an estimate of joint entropy, such as the inverse compression ratio, which in turn is used to determine the presence of seizure in the EEG signal. In numerous embodiments, seizure detectors continuously obtain EEG signals which are processed using a sliding window in order to provide continuous detection capabilities. However, existing seizure detectors only process one dimension of EEG signals at a time to determine the presence of seizure.

Figure 2:
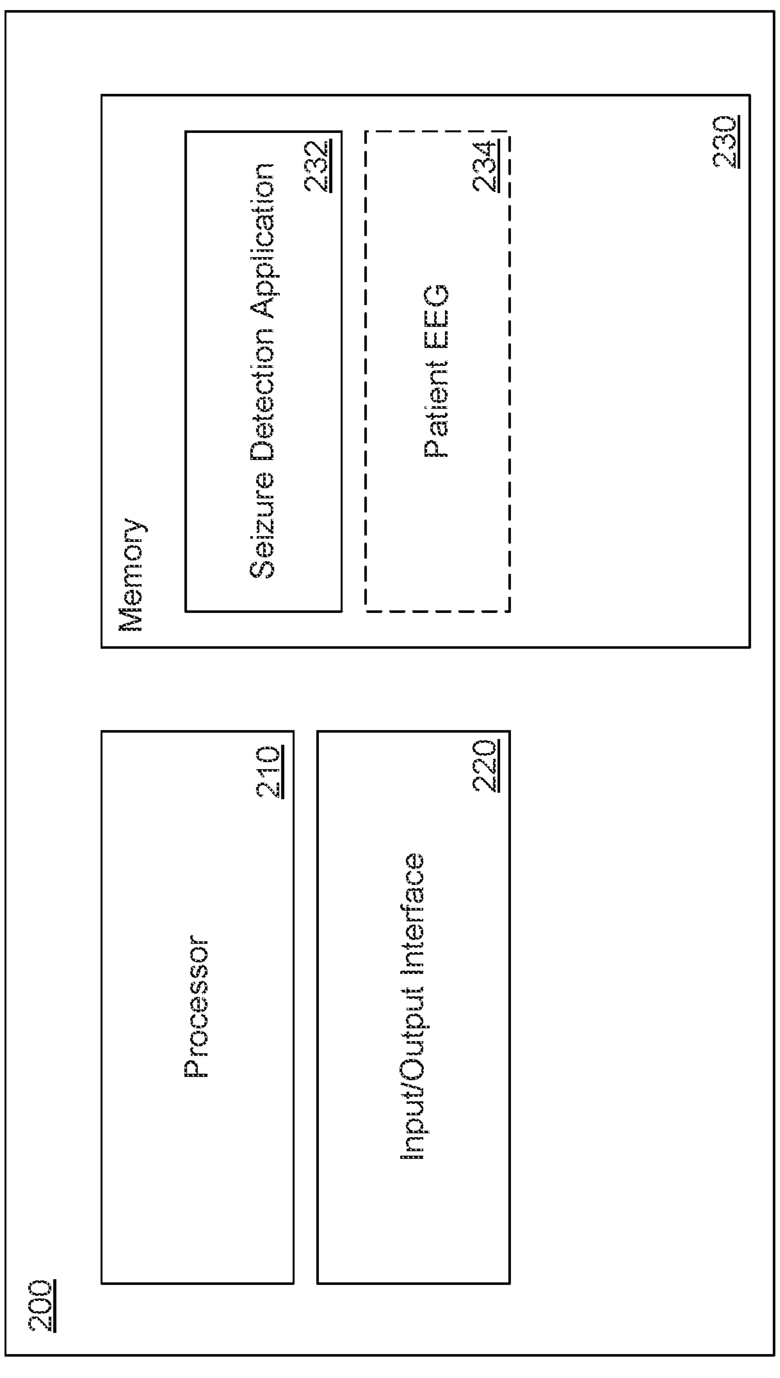
FIG. 2 is a seizure detector in accordance with an embodiment of the invention.

Turning now to FIG. 2, a block diagram for a seizure detector in accordance with an embodiment of the invention is illustrated. Seizure detector 200 includes a processor 210. Processors are any processing circircuitry or combination of processing circuitries capable of processing EEG signals and calculating an ICR metric, and subsequently detecting seizure based on the ICR metric. Processors can include, but are not limited to, central processing units (CPUs), graphics processing units (GPUs), application-specific integrated circuits (ASICs), field-programmable gate arrays (FPGAs), and/or any other processing circuits as appropriate to the requirements of specific applications of embodiments of the invention. Seizure detector 200 further includes an input/output (I/O) interface 220. I/O interfaces are capable of receiving data from and transmitting data to other devices such as (but not limited to) EEG devices and treatment devices.

Seizure detector 200 additionally includes a memory 230. The memory is a machine-readable medium for storing instructions capable of configuring the processor to perform specific processes. The memory can be made of volatile and/or non-volatile memory. The memory 230 contains a seizure detection application 232 which configures the processor 210 to carry out various seizure detection processes as described herein. The memory 230 can also store patient EEG signals for processing.

While a particular architecture for a seizure detector is illustrated in FIG. 2, as can be readily appreciated, different architectures can be used such as (but not limited to) those that utilize distributed computing architectures or any other computing architecture, as appropriate to the requirements of specific applications of embodiments of the invention. Seizure detection processors using the ICR metric are described below.

Seizure Detection Using Inverse Compression Ratio

As discussed above, periods of seizure activity have different amounts of joint entropy in the corresponding EEG signal than periods of non-seizure activity. From this, it is expected that seizures would exhibit a global change in joint entropy across multielectrode EEG due to the complex interconnections between neurons and network effects. However, calculating the joint entropy for high-dimensional signals is combinatorically intractable with a prohibitively high computational cost because it requires calculating the mutual information of all combinations of every group of dimensions of all sizes. In other words, for n-dimensional data, $$\sum_{m=1}^{n}\binom{n}{m}$$

total sets of mutual information would need to be computed. Diverse strategies for estimating joint entropy have been developed as workarounds, however these still tend to have high computational cost and are not accurate estimates. Systems and methods described herein utilize inverse compression ratio as a method to estimate the unbiased upper bound of joint entropy as a qEEG method for seizure detection.

By definition, entropy represents the amount of information in a signal; thus, entropy must be less than the compressed size for a losslessly encoded compressed signal. The same inequality extends for joint entropy, and lossless compression algorithms can serve as an efficient way to calculate this upper bound on joint entropy for multidimensional signals. The normalized, unitless measure of ICR can be calculated by dividing both joint entropy (JE) and compressed size (CS) by raw size (RS), allowing direct comparisons of signal complexity across time, and to first-order, participants:

$$\frac{JE}{RS} \leq \frac{CS}{RS} = ICR$$

The inverse compression ratio, a qEEG method for seizure detection, positively correlates with joint entropy: a signal with high information content (large entropy) requires more bits to losslessly represent the data (large compressed size). In other words, compression can identify patterns in data to efficiently store all of its information with less storage space; consequently, a signal with high regularity results in low compressed size and ICR. Therefore, lossless data compression algorithms which perfectly reconstruct the original information by preserving all values and their locations while making no assumptions about their data structure can be leveraged to calculate ICR.

Due to its permutation sensitivity and generalized nature that allow for multidimensional estimations, ICR can safely be computed over the full electrode set without losing electrode structure. Furthermore, any number of different lossless compression algorithms can be used to calculate ICR, many of which are highly optimized for particular computing platforms. In numerous embodiments, the DEFLATE algorithm is used (such as the implementation found in gzip). However, any number of different lossless compression algorithms can be used such as (but not limited to) Lempel-Ziv-Welch, Asymmetrical Numeral Systems (ANS) compression, Free Lossless Audio Codec (FLAC), portable network graphics (PNG), Burrows-Wheeler compression (e.g. bz2), Lempel-Ziv-Markov chain algorithm compression, and/or any other lossless compression algorithm as appropriate to the requirements of specific applications of embodiments of the invention. As can be readily appreciated, the form of the EEG signal can be stored as appropriate to the requirements of the selected lossless compression algorithm.

Seizure detection is a binary classification of time windows between seizure and non-seizure states. Thus, time periods with ICR measurements above a predetermined threshold are treated as seizure events, and other time periods below the threshold are treated as non-seizure activity. In many embodiments, the time period window is 1 second. However, windows between approximately 1 second to 5 seconds can be used. As can be readily appreciated, the window can be extended to be longer than 5 seconds (windows of 20 or 30 seconds can be used), although doing so may reduce the responsiveness of the detection as data needs to be collected for the given window for real-time applications. In some embodiments, a sliding window can be used to attempt to mitigate the reduction in responsiveness. For batch analysis purposes such as physician review, longer windows may be preferable.

Figure 3:
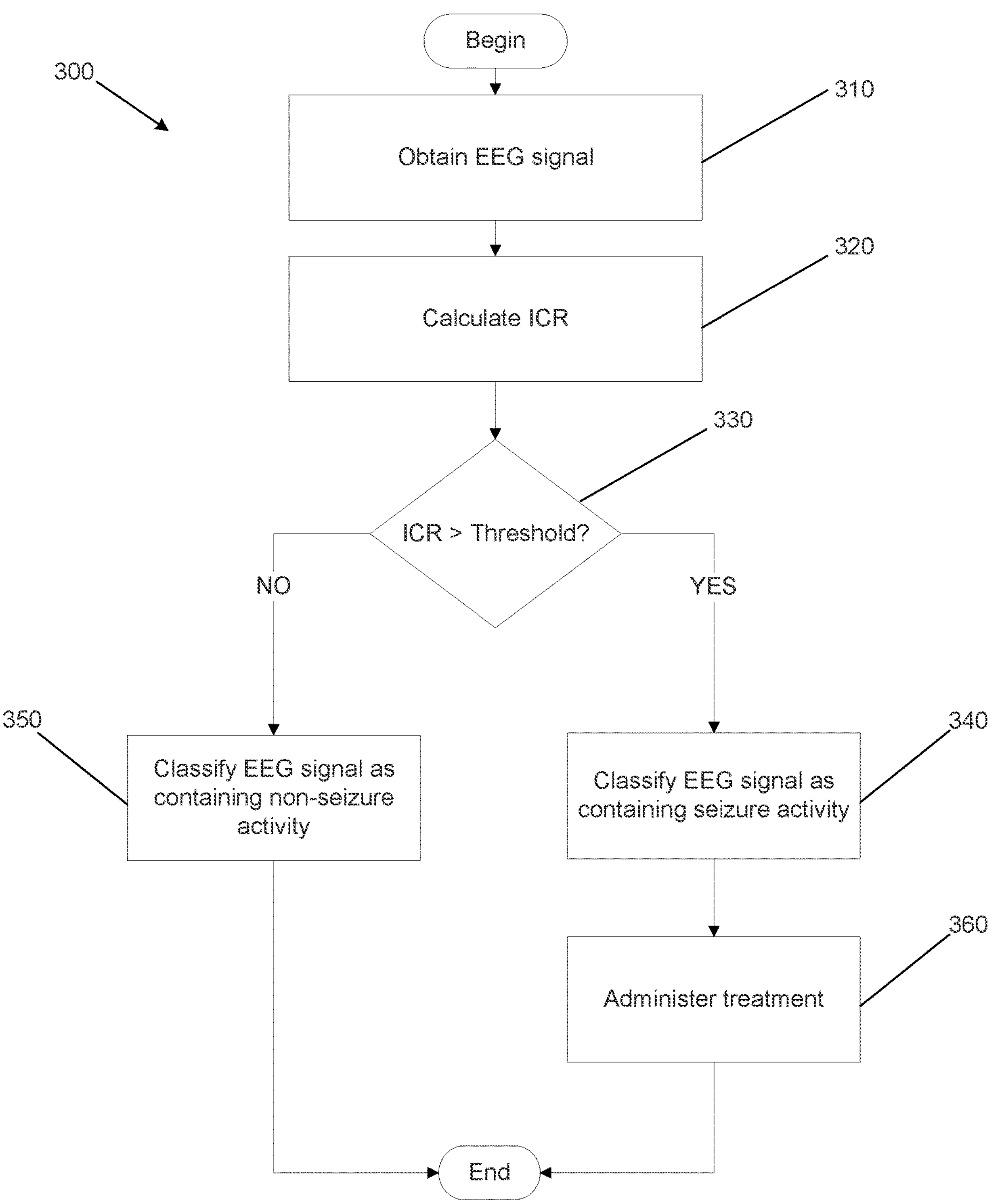
FIG. 3 is a flow chart for a seizure detection process in accordance with an embodiment of the invention.

Turning now to FIG. 3, a process for detecting seizures in accordance with an embodiment of the invention is illustrated. Process 300 includes obtaining (310) an EEG signal from an EEG device. The ICR is calculated (320) for the EEG signal. If the ICR is greater (330) than a classification threshold, then the EEG signal is classified (340) as containing seizure activity. Otherwise, the EEG signal is classified (350) as non-seizure activity. If the EEG signal contains seizure activity, a treatment can be automatically administered (360) via a treatment device in order to attempt to halt the seizure. In numerous embodiments, this process is continuously performed as new EEG data is received. In some embodiments, the data and/or ICR measurements are stored. As can be readily appreciated, FIG. 3 illustrates only one of many processes, and other steps can be performed or not performed as appropriate to the requirements of specific applications of embodiments of the invention. For example, EEG data does not need to be labeled, and steps can be taken just based on the ICR value. In some embodiments, warnings are delivered instead of treatment administration. Additionally, in many embodiments, a machine learning model can be trained on a training data set that contains ICR values and associated ground-truth classifications of associated seizure for a given EEG signal window size. This machine learning model can be used instead of, or in concert with a threshold metric, to classify EEG signals as containing seizure activity. Further, many different methods can be used to set the classification threshold.

In order to set the classification threshold, sample EEG data for the patient can be collected for determining a baseline ICR for a given patient. Brains are idiosyncratic, and different patients may have different baseline ICRs. The threshold can be defined as a value significantly greater than the baseline ICR. In some embodiments, the threshold is more than 1 standard deviation above baseline ICR. In various embodiments, the threshold is a multiple of the root-mean-square (RMS) of the signal. In some embodiments, the threshold is more than between 1 and 3 standard deviations above baseline ICR.

Seizure analysis is performed on unbalanced data: that is the prevalence of events defined as $$\frac{P}{P+N},$$

where P and N are the number of positive and negative events, respectively, is close to 0. A problem for binary classification of rare events is that an unintelligent classifier that always detects non-occurrence may achieve high performance. To resolve this, in various embodiments, performance metrics that prioritizes the correct detection of seizure events are used. Some examples are precision-recall (PR) curve and F1 score. Classifier performance can be calculated based on a confusion matrix containing the number of true positives (TP), true negatives (TN), false positives (FP), and false negatives (FN) using epileptologist-identified seizure times as ground truth labels. The PR curve plots precision (i.e., positive predictive value) vs. recall (i.e., sensitivity) over all possible threshold values, and its area is a threshold independent composite score that reflects the classifier's ability to detect events. PPV is calculated as $$PPV = \frac{TP}{TP+FP},$$

and sensitivity is calculated as $$SE = \frac{TP}{TP+FN}.$$

The F1 score is the harmonic mean of PPV and SE which is calculated as $$\frac{PPV \times SE}{PPV+SE}.$$

Although specific systems and methods for seizure detection are discussed above, many different methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. An automated seizure treatment system, comprising:

an electroencephalogram (EEG) device configured to record neural activity from a brain of a patient;

a treatment device;

a processor; and a memory, the memory containing a seizure detection application that configures the processor to:

obtain an EEG signal from the EEG device;

calculate an inverse compression ratio based on the EEG signal, wherein calculating the inverse compression ratio comprises:

measuring an uncompressed size of the EEG signal;

compressing the EEG signal using a lossless compression algorithm;

measuring a compressed size of the EEG signal; and dividing the compressed size by the uncompressed size; and when the inverse compression ratio is greater than a classification threshold, automatically deliver treatment capable of stopping the seizure to the patient using the treatment device.

2. The system of claim 1, wherein the EEG device is a stereo EEG device.

3. The system of claim 1, wherein the EEG device is a scalp EEG device.

4. The system of claim 1, wherein the EEG device is an electrocorticogram (ECoG) device.

5. The system of claim 1, wherein the treatment device is an implantable neurostimulator configured to produce neurostimulation to counteract the spread of seizure activity in the brain of the patient.

6. The system of claim 1, wherein the treatment device is a drug pump configured to deliver an anti-seizure drug.

7. The system of claim 1, wherein the treatment device further comprises a warning device capable of producing an alert indicating seizure activity.

8. The system of claim 1, wherein the classification threshold is a value selected to maximize an F1 score for a precision recall curve generated using historical EEG signals from the brain of the patient.

9. The system of claim 1, wherein the lossless compression algorithm is the DEFLATE algorithm.

10. An automated seizure treatment method, comprising:

obtaining an electroencephalogram (EEG) signal from an EEG device configured to record neural activity from a brain of a patient;

calculating, using a processor, an inverse compression ratio based on the EEG signal using a seizure detector, wherein calculating the inverse compression ratio comprises:

measuring an uncompressed size of the EEG signal;

compressing the EEG signal using a lossless compression algorithm;

measuring a compressed size of the EEG signal; and dividing the compressed size by the uncompressed size; and when the inverse compression ratio is greater than a classification threshold, automatically delivering treatment capable of stopping the seizure to the patient using the treatment device.

11. The method of claim 10, wherein the EEG device is a stereo EEG device.

12. The method of claim 10, wherein the EEG device is a scalp EEG device.

13. The method of claim 10, wherein the EEG device is an electrocorticogram (ECoG) device.

14. The method of claim 10, wherein the treatment device is an implantable neurostimulator configured to produce neurostimulation to counteract the spread of seizure activity in the brain of the patient.

15. The method of claim 1, wherein the treatment device is a drug pump configured to deliver an anti-seizure drug.

16. The method of claim 10, wherein the treatment device further comprises a warning device capable of producing an alert indicating seizure activity.

17. The method of claim 10, wherein the classification threshold is a value selected to maximize an F1 score for a precision recall curve generated using historical EEG signals from the brain of the patient.

18. The method of claim 10, wherein the lossless compression algorithm is the DEFLATE algorithm.

* * * * *